United States Patent
Fan et al.

(10) Patent No.: US 8,586,535 B2
(45) Date of Patent: Nov. 19, 2013

(54) HUMANIZED RECOMBINANT URICASE AND MUTANTS THEREOF

(75) Inventors: Kai Fan, Jiulongpo Chongqing (CN); Chun Zhang, Jiulongpo Chongqing (CN); Xuefeng Ma, Jiulongpo Chongqing (CN); Xiang Mei, Jiulongpo Chongqing (CN); Chunlan Hu, Jiulongpo Chongqing (CN)

(73) Assignee: Chongqing Fagen Biomedical Inc., Jiulongpo Chongqing (CN)

( * ) Notice: Subject to any disclaimer, the term of this patent is extended or adjusted under 35 U.S.C. 154(b) by 0 days.

(21) Appl. No.: 13/504,065

(22) PCT Filed: Mar. 12, 2010

(86) PCT No.: PCT/CN2010/071020
§ 371 (c)(1),
(2), (4) Date: Jun. 22, 2012

(87) PCT Pub. No.: WO2011/050599
PCT Pub. Date: May 5, 2011

(65) Prior Publication Data
US 2012/0269795 A1    Oct. 25, 2012

(30) Foreign Application Priority Data
Oct. 27, 2009    (CN) .......................... 2009 1 0191240

(51) Int. Cl.
*A61K 38/00*    (2006.01)
*C07K 1/00*    (2006.01)
*C12N 9/06*    (2006.01)

(52) U.S. Cl.
USPC .......................... 514/12.1; 435/191; 530/350

(58) Field of Classification Search
USPC .......................... 435/191; 514/12.1; 530/350
See application file for complete search history.

(56) References Cited

U.S. PATENT DOCUMENTS 6,576,235 B1 *  6/2003  Williams et al. ............. 424/94.4
7,056,713 B1    6/2006  Hershfield et al.

FOREIGN PATENT DOCUMENTS

| CN | 1322243 | 11/2001 |
| CN | 101194016 | 6/2008 |
| CN | 101198693 | 6/2008 |

OTHER PUBLICATIONS

International Search Report of International Application No. PCT/CN2010/071020, mailed Jul. 15, 2010.
Ganson, N. J. et al., "Control of hyperuricemia in subjects with refractory gout, and induction of antibody against poly (ethylene glycol) (PEG), in a phase I trial of subcutaneous PEGylated urate oxidase", Arthritis Research & Therapy, 2006, vol. 8, No. 1, pp. 1-10.
Retailleau, P. et al., "Complexed and ligand-free high-resolution structures of urate oxidase (Uox) from *Aspergillus flavus*: a reassignment of the active-site binding mode", Acta Cryst., Biological Crystallography, 2004, D60, pp. 453-462.
Junjie, Y. et al., "Homology modeling and bioinformatics analysis of three-dimensional structure of human urate oxidase", Computers and Applied Chemistry, 2007, vol. 24, No. 12, pp. 1643-1646.
Lee, C. C. et al., "Generation of cDNA Probes Directed by Amino Acid Sequence: Cloning of Urate Oxidase", Science, Mar. 11, 1988, vol. 239, pp. 1288-1291.
Huang, S-H. et al., "Modified colorimetric assay for uricase activity and a screen for mutant *Bacillus subtilis* uricase genes following StEP mutagenesis", Eur. J. Biochem., 2004, vol. 271, pp. 517-523.
Suzuki, K. et al., "Molecular Cloning and Expression of Uricase Gene from Arthrobacter globiformis in *Escherichia coli* and Characterization of the Gene Product", Journal of Bioscience and Bioengineering, 2004, vol. 98, No. 3, pp. 153-158.
Jones, D. P. et al., "Renal Dysfunction and Hyperuricemia at Presentation and Relapse of Acute Lymphoblastic Leukemia", Medical and Pediatric Oncology, 1990, vol. 18, pp. 283-286.
Bayol, A. et al., "Study of pH and temperature-induced transitions in urate oxidase (Uox-EC1.7.3.3) by microcalorimetry (DSC), size exclusion chromatography (SEC) and enzymatic activity experiments", Biophysical Chemistry, 1995, vol. 54, pp. 229-235.
Shunle, C. et al., "The epidemiology study of hyperuricemia and gout in a community population of Huangpu District in Shanghai", Chinese Medical Journal, 1998, vol. 111, No. 3, pp. 228-230.
Emmerson, B. T., "The Management of Gout", The New England Journal of Medicine, Feb. 15, 1996, vol. 334, No. 7, pp. 445-451.
Wu, X. et al., "Two Independent Mutational Events in the Loss of Urate Oxidase during Hominoid Evolution", Journal of Molecular Evolution, 1992, vol. 34, pp. 78-84.
Pui, C-H, et al., "Urate oxidase in prevention and treatment of hyperuricemia associated with lymphoid malignancies", Leukemia, 1997, vol. 11, pp. 1813-1816.
Wu, X. et al., "Urate oxidase: Primary structure and evolutionary implications", Proc. Natl. Acad. Sci., 1989, vol. 86, pp. 9412-9416.

* cited by examiner

*Primary Examiner* — Maryam Monshipouri
(74) *Attorney, Agent, or Firm* — Ping Wang; Andrews Kurth LLP

(57) ABSTRACT

The present invention provides a humanized recombinant uricase and mutants thereof, wherein the humanized recombinant uricase is a chimeric protein which comprises amino acids of non-human mammal uricase and amino acids of human uricase. The humanized recombinant unease and mutants thereof have reduced immunogenicity in human, and can be used for the treatment of hyperuricemia and gout.

17 Claims, 5 Drawing Sheets

```
                   *        20         *        40         *        60         *
BOVINE : MAHYHNDYQKNDEVEFVRTGYGKDMVKVLHIQRDGKYHSIKEVATSVQLTLNSRREYLHGDNSDIIPTDTIKNTVQ :  76
DOG    : MAHYHNDYKKNDEVEFVRTGYGKDMVKVLHIQRDGKYHSIKEVATSVQLTLSSKKDYVYGDNSDIIPTDTIKNTVH :  76
HUMAN  : MAHYHNNYKKNDEVEFVRTGYGKEMVKVLHIQRDGKYHSIKEVATSVQLTLSSKKDYLHGDNSDIIPTDTIKNTVH :  76
PIG    : MAHYRNDYKKNDEVEFVRTGYGKDMIKVLHIQRDGKYHSIKEVATSVQLTLSSKKDYLHGDNSDVIPTDTIKNTVN :  76

80        *       100         *       120         *       140         *
BOVINE : VLAKFKGIKSIETFAMNICEHFLSSFNHVIRVQVYVEEVPWKRFEKNGVKHVHAFIHTPTGTHFCEVEQLRSGPPV : 152
DOG    : VLAKFKGIKSIETFAMNICEHFLSSFNHVIRAQVYVEEVPWKRFEKNGVKHVHAFIHNPTGTHFCEVEQMRSGPPV : 152
HUMAN  : VLAKFKEIKSIEAFYVNICEHFLSSFNHVIRAQVYMEEIPWKHLEKNEVKHVHAFIHTPTGTHFCEVEQLRSGPQV : 152
PIG    : VLAKFKGIKSIETFAVTICEHFLSSFKHVIRAQVYVEEVPWKRFEKNGVKHVHAFIYTPTGTHFCEVEQIRNGPPV : 152

160         *       180         *       200         *       220
BOVINE : IHSGIKDLKVLKTTQSGFEGFLKDQFTTLPEVKDRCFATQVYCKWRYHQGRDVDFEATWEAVRGIVLKKFAGPYDK : 228
DOG    : IHSGIKDLKVLKTTQSGFEGFIKDQFTTLPEVKDRCFATKVYCKWRYHQGRDVDFEATWDTVRDIVLERFAGPYDK : 228
HUMAN  : IHSGIKDLKVLKTTQSGFEGFIKDQFTTLPEVKDRCFATQVYCKWRYHQCRDVDFKATWDTIRDLVMEKSAGPYDK : 228
PIG    : IHSGIKDLKVLKTTQSGFEGFIKDQFTTLPEVKDRCFATQVYCKWRYHQGRDVDFEATWDTVRSIVLQKFAGPYDK : 228

*       240         *       260         *       280         *       300
BOVINE : GEYSPSVQKTLYDIQVLSLSQLPEIEDMEISLPNIHYFNIDMSKMGLINKEEVLLPLDNPYGRITGTVKRKLTSRL : 304
DOG    : GEYSPSVQKTLYDIQVHSLSRVPEMEDMEISLPNIHYFNIDMSKMGLINKEEVLLPLDNPYGRITGTAKRKLASKL : 304
HUMAN  : GEYLTSVQKTLCDIQVLSLSRVPAIEDMEISLPNIHYFNIDMSKMGLINKEEVLLPLDNPYGRITGTVKRKLSSRL : 304
PIG    : GEYSPSVQKTLYDIQVLTLGQVPEIEDMEISLPNIHYINIDMSKMGLINKEEVLLPLDNPYGRITGTVKRKLTSRL : 304
```

Fig. 1

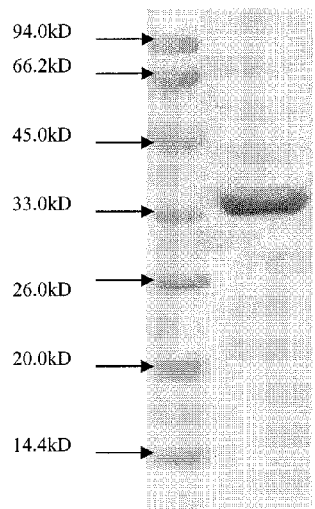
A
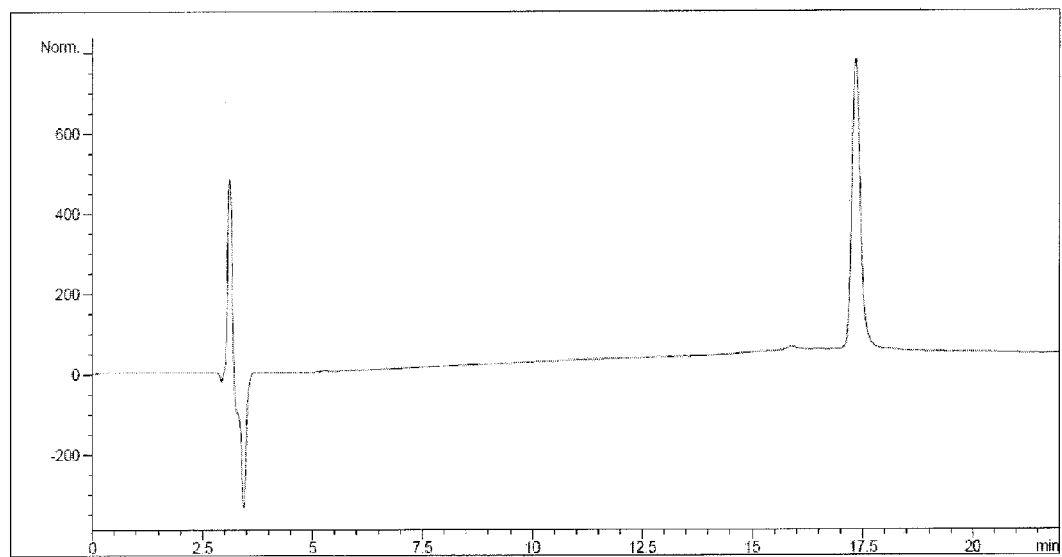
B
Fig. 4

SEQUENCE LISTING

<160> NUMBER OF SEQ ID NOS: 21

<210> SEQ ID NO 1
<211> LENGTH: 304
<212> TYPE: PRT
<213> ORGANISM: Homo sapiens

<400> SEQUENCE: 1

Met Ala His Tyr His Asn Asn Tyr Lys Lys Asn Asp Glu Val Glu Phe
1               5                   10                  15

Val Arg Thr Gly Tyr Gly Lys Glu Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Glu Ile Lys Ser Ile Glu Ala Phe Gly Val Asn Ile Cys Glu
                85                  90                  95

His Phe Leu Ser Ser Phe Asn His Val Ile Arg Ala Gln Val Tyr Met
            100                 105                 110

Glu Glu Ile Pro Trp Lys His Leu Glu Lys Asn Glu Val Lys His Val
        115                 120                 125

His Ala Phe Ile His Thr Pro Thr Gly Thr His Phe Cys Glu Val Glu
    130                 135                 140

Gln Leu Arg Ser Gly Pro Gln Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Lys
        195                 200                 205

Ala Thr Trp Asp Thr Ile Arg Asp Leu Val Met Glu Lys Ser Ala Gly
    210                 215                 220

Pro Tyr Asp Lys Gly Glu Tyr Leu Thr Ser Val Gln Lys Thr Leu Cys
225                 230                 235                 240

Asp Ile Gln Val Leu Ser Leu Ser Arg Val Pro Ala Ile Glu Asp Met
                245                 250                 255

Glu Ile Ser Leu Pro Asn Ile His Tyr Phe Asn Ile Asp Met Ser Lys
            260                 265                 270

```
Met Gly Leu Ile Asn Lys Glu Glu Val Leu Pro Leu Asp Asn Pro
        275                 280                 285

Tyr Gly Lys Ile Thr Gly Thr Val Lys Arg Lys Leu Ser Ser Arg Leu
        290                 295                 300
```

<210> SEQ ID NO 2
<211> LENGTH: 304
<212> TYPE: PRT
<213> ORGANISM: Sus scrofa

<400> SEQUENCE: 2

```
Met Ala His Tyr Arg Asn Asp Tyr Lys Lys Asn Asp Glu Val Glu Phe
  1               5                  10                  15

Val Arg Thr Gly Tyr Gly Lys Asp Met Ile Lys Val Leu His Ile Gln
             20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
     50                  55                  60

Val Ile Pro Thr Asp Thr Ile Lys Asn Thr Val Asn Val Leu Ala Lys
 65                  70                  75                  80

Phe Lys Gly Ile Lys Ser Ile Glu Thr Phe Ala Val Thr Ile Cys Glu
                 85                  90                  95

His Phe Leu Ser Ser Phe Lys His Val Ile Arg Ala Gln Val Tyr Val
            100                 105                 110

Glu Glu Val Pro Trp Lys Arg Phe Gly Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Arg Ile Thr Gly Thr Val Lys Arg Lys Leu Thr Ser Arg Leu
    290                 295                 300
```

<210> SEQ ID NO 3
<211> LENGTH: 304
<212> TYPE: PRT
<213> ORGANISM: Canis familiaris

<400> SEQUENCE: 3

```
Met Ala His Tyr His Asn Asp Tyr Lys Lys Asn Asp Glu Val Glu Phe
```

-continued

```
               1               5                  10                 15
            Val Arg Thr Gly Tyr Gly Lys Asp Met Val Lys Val Leu His Ile Gln
                          20                 25                 30

Arg Asp Gly Lys Tyr His Ser Ile Lys Glu Val Ala Thr Ser Val Gln
                          35                 40                 45

Leu Thr Leu Ser Ser Lys Lys Asp Tyr Val Tyr Gly Asp Asn Ser Asp
                          50                 55                 60

Ile Ile Pro Thr Asp Thr Ile Lys Asn Thr Val His Val Leu Ala Lys
             65                 70                 75                 80

Phe Lys Gly Ile Lys Ser Ile Glu Thr Phe Ala Met Asn Ile Cys Glu
                          85                 90                 95

His Phe Leu Ser Ser Phe Asn His Val Ile Arg Ala Gln Val Tyr Val
                          100                105                110

Glu Val Pro Trp Lys Arg Phe Glu Lys Asn Gly Val Lys His Val
                          115                120                125

His Ala Phe Ile His Asn Pro Thr Gly Thr His Phe Cys Glu Val Glu
                          130                135                140

Gln Met Arg Ser Gly Pro Pro Val Ile His Ser Gly Ile Lys Asp Leu
            145                150                155                160

Lys Val Leu Lys Thr Thr Gln Ser Gly Phe Glu Gly Phe Ile Lys Asp
                          165                170                175

Gln Phe Thr Thr Leu Pro Glu Val Lys Asp Arg Cys Phe Ala Thr Lys
                          180                185                190

Val Tyr Cys Lys Trp Arg Tyr His Gln Gly Arg Asp Val Asp Phe Glu
                          195                200                205

Ala Thr Trp Asp Thr Val Arg Asp Ile Val Leu Glu Lys Phe Ala Gly
                          210                215                220

Pro Tyr Asp Lys Gly Glu Tyr Ser Pro Ser Val Gln Lys Thr Leu Tyr
            225                230                235                240

Asp Ile Gln Val His Ser Leu Ser Arg Val Pro Glu Met Glu Asp Met
                          245                250                255

Glu Ile Ser Leu Pro Asn Ile His Tyr Phe Asn Ile Asp Met Ser Lys
                          260                265                270

Met Gly Leu Ile Asn Lys Glu Glu Val Leu Leu Pro Leu Asp Asn Pro
                          275                280                285

Tyr Gly Arg Ile Thr Gly Thr Ala Lys Arg Lys Leu Ala Ser Lys Leu
                          290                295                300

<210> SEQ ID NO 4
<211> LENGTH: 304
<212> TYPE: PRT
<213> ORGANISM: Bos taurus

<400> SEQUENCE: 4

Met Ala His Tyr His Asn Asp Tyr Gln Lys Asn Asp Glu Val Glu Phe
            1               5                  10                 15

Val Arg Thr Gly Tyr Gly Lys Asp Met Val Lys Val Leu His Ile Gln
                          20                 25                 30

Arg Asp Gly Lys Tyr His Ser Ile Lys Glu Val Ala Thr Ser Val Gln
                          35                 40                 45

Leu Thr Leu Asn Ser Arg Arg Glu Tyr Leu His Gly Asp Asn Ser Asp
                          50                 55                 60

Ile Ile Pro Thr Asp Thr Ile Lys Asn Thr Val Gln Val Leu Ala Lys
             65                 70                 75                 80

Phe Lys Gly Ile Lys Ser Ile Glu Thr Phe Ala Met Asn Ile Cys Glu
```

```
                       85                  90                  95
His Phe Leu Ser Ser Phe Asn His Val Ile Arg Val Gln Val Tyr Val
                100                 105                 110
Glu Glu Val Pro Trp Lys Arg Phe Glu Lys Asn Gly Val Lys His Val
                115                 120                 125
His Ala Phe Ile His Thr Pro Thr Gly Thr His Phe Cys Glu Val Glu
            130                 135                 140
Gln Leu Arg Ser Gly Pro Pro Val Ile His Ser Gly Ile Lys Asp Leu
145                 150                 155                 160
Lys Val Leu Lys Thr Thr Gln Ser Gly Phe Glu Gly Phe Leu Lys Asp
                165                 170                 175
Gln Phe Thr Thr Leu Pro Glu Val Lys Asp Arg Cys Phe Ala Thr Gln
            180                 185                 190
Val Tyr Cys Lys Trp Arg Tyr His Gln Gly Arg Asp Val Asp Phe Glu
                195                 200                 205
Ala Thr Trp Glu Ala Val Arg Gly Ile Val Leu Lys Lys Phe Ala Gly
            210                 215                 220
Pro Tyr Asp Lys Gly Glu Tyr Ser Pro Ser Val Gln Lys Thr Leu Tyr
225                 230                 235                 240
Asp Ile Gln Val Leu Ser Leu Ser Gln Leu Pro Glu Ile Glu Asp Met
                245                 250                 255
Glu Ile Ser Leu Pro Asn Ile His Tyr Phe Asn Ile Asp Met Ser Lys
            260                 265                 270
Met Gly Leu Ile Asn Lys Glu Glu Val Leu Leu Pro Leu Asp Asn Pro
            275                 280                 285
Tyr Gly Arg Ile Thr Gly Thr Val Lys Arg Lys Leu Thr Ser Arg Leu
            290                 295                 300

<210> SEQ ID NO 5
<211> LENGTH: 304
<212> TYPE: PRT
<213> ORGANISM: Artificial Sequence
<220> FEATURE:
<223> OTHER INFORMATION: Chimeric dog-human uricase (UHC) with aa 1-240
      from dog uricase and aa 241-304 from human uricase

<400> SEQUENCE: 5

Met Ala His Tyr His Asn Asp Tyr Lys Lys Asn Asp Glu Val Glu Phe
1               5                   10                  15
Val Arg Thr Gly Tyr Gly Lys Asp Met Val Lys Val Leu His Ile Gln
                20                  25                  30
Arg Asp Gly Lys Tyr His Ser Ile Lys Glu Val Ala Thr Ser Val Gln
            35                  40                  45
Leu Thr Leu Ser Ser Lys Lys Asp Tyr Val Tyr Gly Asp Asn Ser Asp
        50                  55                  60
Ile Ile Pro Thr Asp Thr Ile Lys Asn Thr Val His Val Leu Ala Lys
65                  70                  75                  80
Phe Lys Gly Ile Lys Ser Ile Glu Thr Phe Ala Met Asn Ile Cys Glu
                85                  90                  95
His Phe Leu Ser Ser Phe Asn His Val Ile Arg Ala Gln Val Tyr Val
                100                 105                 110
Glu Glu Val Pro Trp Lys Arg Phe Glu Lys Asn Gly Val Lys His Val
                115                 120                 125
His Ala Phe Ile His Asn Pro Thr Gly Thr His Phe Cys Glu Val Glu
            130                 135                 140
Gln Met Arg Ser Gly Pro Pro Val Ile His Ser Gly Ile Lys Asp Leu
```

```
                145                 150                 155                 160
Lys Val Leu Lys Thr Thr Gln Ser Gly Phe Glu Gly Phe Ile Lys Asp
                    165                 170                 175

Gln Phe Thr Thr Leu Pro Glu Val Lys Asp Arg Cys Phe Ala Thr Lys
                    180                 185                 190

Val Tyr Cys Lys Trp Arg Tyr His Gln Gly Arg Asp Val Asp Phe Glu
                    195                 200                 205

Ala Thr Trp Asp Thr Val Arg Asp Ile Val Leu Glu Lys Phe Ala Gly
                    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Ala Ile Glu Asp Met
                    245                 250                 255

Glu Ile Ser Leu Pro Asn Ile His Tyr Phe Asn Ile Asp Met Ser Lys
                    260                 265                 270

Met Gly Leu Ile Asn Lys Glu Glu Val Leu Leu Pro Leu Asp Asn Pro
                    275                 280                 285

Tyr Gly Lys Ile Thr Gly Thr Val Lys Arg Lys Leu Ser Ser Arg Leu
                    290                 295                 300

<210> SEQ ID NO 6
<211> LENGTH: 304
<212> TYPE: PRT
<213> ORGANISM: Artificial Sequence
<220> FEATURE:
<223> OTHER INFORMATION: Chimeric dog-human uricase (UHC) with Leu245
      replaced by S246T-S248G-R249Q

<400> SEQUENCE: 6

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
                    20                  25                  30

Arg Asp Gly Lys Tyr His Ser Ile Lys Glu Val Ala Thr Ser Val Gln
                    35                  40                  45

Leu Thr Leu Ser Ser Lys Lys Asp Tyr Val Tyr Gly Asp Asn Ser Asp
                    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                    85                  90                  95

His Phe Leu Ser Ser Phe Asn His Val Ile Arg Ala Gln Val Tyr Val
                    100                 105                 110

Glu Glu Val Pro Trp Lys Arg Phe Glu Lys Asn Gly Val Lys His Val
                    115                 120                 125

His Ala Phe Ile His Asn Pro Thr Gly Thr His Phe Cys Glu Val Glu
                    130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                    165                 170                 175

Gln Phe Thr Thr Leu Pro Glu Val Lys Asp Arg Cys Phe Ala Thr Lys
                    180                 185                 190

Val Tyr Cys Lys Trp Arg Tyr His Gln Gly Arg Asp Val Asp Phe Glu
                    195                 200                 205

Ala Thr Trp Asp Thr Val Arg Asp Ile Val Leu Glu Lys Phe Ala Gly
```

```
            210                 215                 220
Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Ala Ile Glu Asp Met
                245                 250                 255

Glu Ile Ser Leu Pro Asn Ile His Tyr Phe Asn Ile Asp Met Ser Lys
                260                 265                 270

Met Gly Leu Ile Asn Lys Glu Val Leu Leu Pro Leu Asp Asn Pro
            275                 280                 285

Tyr Gly Lys Ile Thr Gly Thr Val Lys Arg Lys Leu Ser Ser Arg Leu
            290                 295                 300
```

<210> SEQ ID NO 7
<211> LENGTH: 304
<212> TYPE: PRT
<213> ORGANISM: Artificial Sequence
<220> FEATURE:
<223> OTHER INFORMATION: Chimeric dog-human uricase (UHC) with L245H-
    A252E-I253M substitutions

<400> SEQUENCE: 7

```
Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Val Tyr Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

Glu Glu Val Pro Trp Lys Arg Phe Glu Lys Asn Gly Val Lys His Val
    115                 120                 125

His Ala Phe Ile His Asn Pro Thr Gly Thr His Phe Cys Glu Val Glu
130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
    195                 200                 205

Ala Thr Trp Asp Thr Val Arg Asp Ile Val Leu Glu Lys Phe Ala Gly
210                 215                 220

Pro Tyr Asp Lys Gly Glu Tyr Ser Pro Ser Val Gln Lys Thr Leu Tyr
225                 230                 235                 240

Asp Ile Gln Val His Ser Leu Ser Arg Val Pro Glu Met Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
```

```
              275                 280                 285
Tyr Gly Lys Ile Thr Gly Thr Val Lys Arg Lys Leu Ser Ser Arg Leu
    290                 295                 300

<210> SEQ ID NO 8
<211> LENGTH: 304
<212> TYPE: PRT
<213> ORGANISM: Artificial Sequence
<220> FEATURE:
<223> OTHER INFORMATION: Chimeric dog-human uricase (UHC) with S246T-
      S248G-R249Q-F266L substitutions

<400> SEQUENCE: 8

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Val Tyr Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile His Asn Pro Thr Gly Thr His Phe Cys Glu Val Glu
    130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
        195                 200                 205

Ala Thr Trp Asp Thr Val Arg Asp Ile Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Ala Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300

<210> SEQ ID NO 9
<211> LENGTH: 304
<212> TYPE: PRT
<213> ORGANISM: Artificial Sequence
<220> FEATURE:
<223> OTHER INFORMATION: Chimeric dog-human uricase (UHC) with L245H-
```

-continued

A252E-I253M-F266L substitutions

<400> SEQUENCE: 9

```
Met Ala His Tyr His Asn Asp Tyr Lys Lys Asn Asp Glu Val Glu Phe
1               5                   10                  15
Val Arg Thr Gly Tyr Gly Lys Asp Met Val Lys Val Leu His Ile Gln
                20                  25                  30
Arg Asp Gly Lys Tyr His Ser Ile Lys Glu Val Ala Thr Ser Val Gln
            35                  40                  45
Leu Thr Leu Ser Ser Lys Lys Asp Tyr Val Tyr Gly Asp Asn Ser Asp
50                  55                  60
Ile Ile Pro Thr Asp Thr Ile Lys Asn Thr Val His Val Leu Ala Lys
65                  70                  75                  80
Phe Lys Gly Ile Lys Ser Ile Glu Thr Phe Ala Met Asn Ile Cys Glu
                85                  90                  95
His Phe Leu Ser Ser Phe Asn His Val Ile Arg Ala Gln Val Tyr Val
            100                 105                 110
Glu Glu Val Pro Trp Lys Arg Phe Glu Lys Asn Gly Val Lys His Val
        115                 120                 125
His Ala Phe Ile His Asn Pro Thr Gly Thr His Phe Cys Glu Val Glu
130                 135                 140
Gln Met Arg Ser Gly Pro Pro Val Ile His Ser Gly Ile Lys Asp Leu
145                 150                 155                 160
Lys Val Leu Lys Thr Thr Gln Ser Gly Phe Glu Gly Phe Ile Lys Asp
                165                 170                 175
Gln Phe Thr Thr Leu Pro Glu Val Lys Asp Arg Cys Phe Ala Thr Lys
            180                 185                 190
Val Tyr Cys Lys Trp Arg Tyr His Gln Gly Arg Asp Val Asp Phe Glu
        195                 200                 205
Ala Thr Trp Asp Thr Val Arg Asp Ile Val Leu Glu Lys Phe Ala Gly
210                 215                 220
Pro Tyr Asp Lys Gly Glu Tyr Ser Pro Ser Val Gln Lys Thr Leu Tyr
225                 230                 235                 240
Asp Ile Gln Val His Ser Leu Ser Arg Val Pro Glu Met Glu Asp Met
                245                 250                 255
Glu Ile Ser Leu Pro Asn Ile His Tyr Leu Asn Ile Asp Met Ser Lys
            260                 265                 270
Met Gly Leu Ile Asn Lys Glu Glu Val Leu Leu Pro Leu Asp Asn Pro
        275                 280                 285
Tyr Gly Lys Ile Thr Gly Thr Val Lys Arg Lys Leu Ser Ser Arg Leu
    290                 295                 300
```

<210> SEQ ID NO 10
<211> LENGTH: 297
<212> TYPE: PRT
<213> ORGANISM: Artificial Sequence
<220> FEATURE:
<223> OTHER INFORMATION: Chimeric dog-human uricase (UHC) with aa 2-7 and 9 deletions and L245H-A252E-I253M substitutions

<400> SEQUENCE: 10

```
Met Tyr Lys Asn Asp Glu Val Glu Phe Val Arg Thr Gly Tyr Gly Lys
1               5                   10                  15
Asp Met Val Lys Val Leu His Ile Gln Arg Asp Gly Lys Tyr His Ser
                20                  25                  30
Ile Lys Glu Val Ala Thr Ser Val Gln Leu Thr Leu Ser Ser Lys Lys
            35                  40                  45
```

```
Asp Tyr Val Tyr Gly Asp Asn Ser Asp Ile Ile Pro Thr Asp Thr Ile
         50                  55                  60

Lys Asn Thr Val His Val Leu Ala Lys Phe Lys Gly Ile Lys Ser Ile
 65                  70                  75                  80

Glu Thr Phe Ala Met Asn Ile Cys Glu His Phe Leu Ser Ser Phe Asn
                 85                  90                  95

His Val Ile Arg Ala Gln Val Tyr Val Glu Val Pro Trp Lys Arg
             100                 105                 110

Phe Glu Lys Asn Gly Val Lys His Val His Ala Phe Ile His Asn Pro
             115                 120                 125

Thr Gly Thr His Phe Cys Glu Val Glu Gln Met Arg Ser Gly Pro Pro
        130                 135                 140

Val Ile His Ser Gly Ile Lys Asp Leu Lys Val Leu Lys Thr Thr Gln
145                 150                 155                 160

Ser Gly Phe Glu Gly Phe Ile Lys Asp Gln Phe Thr Thr Leu Pro Glu
                165                 170                 175

Val Lys Asp Arg Cys Phe Ala Thr Lys Val Tyr Cys Lys Trp Arg Tyr
                180                 185                 190

His Gln Gly Arg Asp Val Asp Phe Glu Ala Thr Trp Asp Thr Val Arg
            195                 200                 205

Asp Ile Val Leu Glu Lys Phe Ala Gly Pro Tyr Asp Lys Gly Glu Tyr
210                 215                 220

Ser Pro Ser Val Gln Lys Thr Leu Tyr Asp Ile Gln Val His Ser Leu
225                 230                 235                 240

Ser Arg Val Pro Glu Met Glu Asp Met Glu Ile Ser Leu Pro Asn Ile
                245                 250                 255

His Tyr Phe Asn Ile Asp Met Ser Lys Met Gly Leu Ile Asn Lys Glu
            260                 265                 270

Glu Val Leu Leu Pro Leu Asp Asn Pro Tyr Gly Lys Ile Thr Gly Thr
                275                 280                 285

Val Lys Arg Lys Leu Ser Ser Arg Leu
290                 295

<210> SEQ ID NO 11
<211> LENGTH: 301
<212> TYPE: PRT
<213> ORGANISM: Artificial Sequence
<220> FEATURE:
<223> OTHER INFORMATION: Chimeric dog-human uricase (UHC) with aa 302-
      304 deletions and L245H-A252E-I253M substitutions

<400> SEQUENCE: 11

Met Ala His Tyr His Asn Asp Tyr Lys Lys Asn Asp Glu Val Glu Phe
  1               5                  10                  15

Val Arg Thr Gly Tyr Gly Lys Asp Met Val Lys Val Leu His Ile Gln
                 20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Val Tyr Gly Asp Asn Ser Asp
        50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Thr Phe Ala Met Asn Ile Cys Glu
                 85                  90                  95

His Phe Leu Ser Ser Phe Asn His Val Ile Arg Ala Gln Val Tyr Val
            100                 105                 110
```

-continued

```
Glu Glu Val Pro Trp Lys Arg Phe Glu Lys Asn Gly Val Lys His Val
            115                 120                 125
His Ala Phe Ile His Asn Pro Thr Gly Thr His Phe Cys Glu Val Glu
        130                 135                 140
Gln Met Arg Ser Gly Pro Pro Val Ile His Ser Gly Ile Lys Asp Leu
145                 150                 155                 160
Lys Val Leu Lys Thr Thr Gln Ser Gly Phe Glu Gly Phe Ile Lys Asp
                165                 170                 175
Gln Phe Thr Thr Leu Pro Glu Val Lys Asp Arg Cys Phe Ala Thr Lys
            180                 185                 190
Val Tyr Cys Lys Trp Arg Tyr His Gln Gly Arg Asp Val Asp Phe Glu
        195                 200                 205
Ala Thr Trp Asp Thr Val Arg Asp Ile Val Leu Glu Lys Phe Ala Gly
        210                 215                 220
Pro Tyr Asp Lys Gly Glu Tyr Ser Pro Ser Val Gln Lys Thr Leu Tyr
225                 230                 235                 240
Asp Ile Gln Val His Ser Leu Ser Arg Val Pro Glu Met Glu Asp Met
                245                 250                 255
Glu Ile Ser Leu Pro Asn Ile His Tyr Phe Asn Ile Asp Met Ser Lys
            260                 265                 270
Met Gly Leu Ile Asn Lys Glu Glu Val Leu Leu Pro Leu Asp Asn Pro
        275                 280                 285
Tyr Gly Lys Ile Thr Gly Thr Val Lys Arg Lys Leu Ser
        290                 295                 300

<210> SEQ ID NO 12
<211> LENGTH: 294
<212> TYPE: PRT
<213> ORGANISM: Artificial Sequence
<220> FEATURE:
<223> OTHER INFORMATION: Chimeric dog-human uricase (UHC) with aa 2-7, 9
      and 302-304 deletions and L245H-A252E-I253M substitutions

<400> SEQUENCE: 12

Met Tyr Lys Asn Asp Glu Val Glu Phe Val Arg Thr Gly Tyr Gly Lys
1               5                   10                  15
Asp Met Val Lys Val Leu His Ile Gln Arg Asp Gly Lys Tyr His Ser
            20                  25                  30
Ile Lys Glu Val Ala Thr Ser Val Gln Leu Thr Leu Ser Ser Lys Lys
        35                  40                  45
Asp Tyr Val Tyr Gly Asp Asn Ser Asp Ile Ile Pro Thr Asp Thr Ile
    50                  55                  60
Lys Asn Thr Val His Val Leu Ala Lys Phe Lys Gly Ile Lys Ser Ile
65                  70                  75                  80
Glu Thr Phe Ala Met Asn Ile Cys Glu His Phe Leu Ser Ser Phe Asn
                85                  90                  95
His Val Ile Arg Ala Gln Val Tyr Val Glu Glu Val Pro Trp Lys Arg
            100                 105                 110
Phe Glu Lys Asn Gly Val Lys His Val His Ala Phe Ile His Asn Pro
        115                 120                 125
Thr Gly Thr His Phe Cys Glu Val Glu Gln Met Arg Ser Gly Pro Pro
    130                 135                 140
Val Ile His Ser Gly Ile Lys Asp Leu Lys Val Leu Lys Thr Thr Gln
145                 150                 155                 160
Ser Gly Phe Glu Gly Phe Ile Lys Asp Gln Phe Thr Thr Leu Pro Glu
                165                 170                 175
```

-continued

Val Lys Asp Arg Cys Phe Ala Thr Lys Val Tyr Cys Lys Trp Arg Tyr
            180                 185                 190

His Gln Gly Arg Asp Val Asp Phe Glu Ala Thr Trp Asp Thr Val Arg
        195                 200                 205

Asp Ile Val Leu Glu Lys Phe Ala Gly Pro Tyr Asp Lys Gly Glu Tyr
    210                 215                 220

Ser Pro Ser Val Gln Lys Thr Leu Tyr Asp Ile Gln Val His Ser Leu
225                 230                 235                 240

Ser Arg Val Pro Glu Met Glu Asp Met Glu Ile Ser Leu Pro Asn Ile
                245                 250                 255

His Tyr Phe Asn Ile Asp Met Ser Lys Met Gly Leu Ile Asn Lys Glu
        260                 265                 270

Glu Val Leu Leu Pro Leu Asp Asn Pro Tyr Gly Lys Ile Thr Gly Thr
    275                 280                 285

Val Lys Arg Lys Leu Ser
    290

<210> SEQ ID NO 13
<211> LENGTH: 927
<212> TYPE: DNA
<213> ORGANISM: Artificial Sequence
<220> FEATURE:
<223> OTHER INFORMATION: Chimeric dog-human uricase (UHC)

<400> SEQUENCE: 13

```
catatggccc attatcataa tgattataaa aaaaatgatg aagttgaatt tgttcgtacc      60
ggttatggta agatatggt  taaagttctg catattcagc gtgatggtaa atatcattct    120
attaaagaag ttgccacctc tgttcagctg accctgtctt ctaaaaaaga ttatgtttat    180
ggtgataatt ctgatattat tccaaccgat accattaaaa ataccgttca tgttctggcc    240
aaatttaaag gtattaaatc tattgaaacc tttgccatga atatttgtga acattttctg    300
tcttctttta atcatgttat tcgtgcccag gtttatgttg aagaagttcc atggaaacgt    360
tttgaaaaaa atggtgttaa acatgttcat gcctttattc ataatccaac cggtacccat    420
ttttgtgaag ttgaacagat gcgttctggt ccaccagtta ttcattctgg tattaaagat    480
ctgaaagttc tgaaaccac  ccagtctggt tttgaaggtt ttattaaaga tcagtttacc    540
accctgccag aagttaaaga tcgttgtttt gccaccaaag tttattgtaa atggcgttat    600
catcagggtc gtgatgttga ttttgaagcc acctgggata ccgttcgtga tattgttctg    660
gaaaaatttg ccggtcctta tgataaaggt gaatattctc catctgttca gaaaaccctg    720
tatgatattc aggttctgtc tctgtctcgt gttccagcca ttgaagatat ggaaatttct    780
ctgccaaata ttcattattt taatattgat atgtctaaaa tgggtctgat taataaagaa    840
gaagttctgc tgccactgga taatccttat ggtaaaatta ccggtaccgt taaacgtaaa    900
ctgtcttctc gtctgtgata aggatcc                                        927
```

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14

```
cacgacatat ggcccattat cata                                            24
```

```
<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
ggatccttat cacagacgag aa                                              22

<210> SEQ ID NO 16
<211> LENGTH: 42
<212> TYPE: DNA
<213> ORGANISM: Artificial Sequence
<220> FEATURE:
<223> OTHER INFORMATION: Synthetic primer

<400> SEQUENCE: 16
tctctgtctc gtgttccaga aatggaagat atggaaattt ct                        42

<210> SEQ ID NO 17
<211> LENGTH: 42
<212> TYPE: DNA
<213> ORGANISM: Artificial Sequence
<220> FEATURE:
<223> OTHER INFORMATION: Synthetic primer

<400> SEQUENCE: 17
ttctggaaca cgagacagag aatgaacctg aatatcatac ag                        42

<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
ttcattatct gaatattgat atgtctaaaa                                      30

<210> SEQ ID NO 19
<211> LENGTH: 30
<212> TYPE: DNA
<213> ORGANISM: Artificial Sequence
<220> FEATURE:
<223> OTHER INFORMATION: Synthetic primer

<400> SEQUENCE: 19
atcaatattc agataatgaa tatttggcag                                      30

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
cgcatatgta taaaaatgat gaag                                            24

<210> SEQ ID NO 21
<211> LENGTH: 24
<212> TYPE: DNA
<213> ORGANISM: Artificial Sequence
```

```
<220> FEATURE:
<223> OTHER INFORMATION: Synthetic primer

<400> SEQUENCE: 21
gtggatcctt atcaagacag ttta                                              24
```

HUMANIZED RECOMBINANT URICASE AND MUTANTS THEREOF

This application is a 371 of PCT/CN10/71020 filed Mar. 12, 2010 and claims foreign priority to Chinese Application No. 200910191240.3, filed Oct. 27, 2009.

FIELD

The present invention relates to DNA recombinant technology and drug. More specifically, the present invention provides a humanized recombinant uricase and mutants thereof, wherein the humanized recombinant uricase is a chimeric protein which comprises amino acids of non-human mammal uricase and amino acids of human uricase. Also provided are DNA sequence encoding the chimeric protein and mutants thereof, vector comprising the DNA sequence, host cell comprising the vector, method for genetic preparation of the protein, and use of the protein for the treatment of hyperuricemia and gout caused thereby.

BACKGROUND

As a disease caused by purine metabolism disorder, gout is recorded at the 5th century B.C. by Hippocrates of Cos (Emmerson B T, N Engl J Med, 1996, 334; 445-451), with clinical character of hyperuricemia and gouty deposition derived from the sedimentation of urates in subcutaeous, joint, and kidney. Uric acid, the final product of purine metabolism in human bodies, may cause hyperuricemia at the concentration of over 70 mg/L; and 5%-12% of patients with hyperuricemia will eventually suffer from gout. Gouty arthritis is caused by sodium urate with saturated concentration in blood or bursa mucosa, wherein the sodium urate forms microcrystal (Nancy J G et al., Arthritis Res Ther. 2006; 8(1), R12). As time passing, chronic hyperuricemia may also produce crystal of uric acid sediments around joints, soft tissues as well as certain kinds of organs; thereby causing gouty acute arthritis, gouty deposition chronic arthritis and joint deformity. Meanwhile, kidney damage is considered to be the second common clinical manifestation of gout. Chronic hyperuricemia will gradually lead to urate sediment in medulla, kidney tubule and renal interstitium, thereby provoking local inflammation, namely chronic urate nephropathy. Patients suffered from severe hyperuricemia (such as tumors, expecially leukemia and lymphoma) may have great amount of uric acid sediments in collecting duct, pelvis, calices and ureter of the kidney in a short period of time, which will lead to lumen blockage, unuresis and acute kidney failure (also called hyperuricemic nephropathy) (Hershfield M S. Cecil, Textbook of Medicine (20th), 1508-1515). Incomplete treatment of the above disease may further provoke the concurrence of gouty coronary heart disease, hyperlipidemia, etc.

With changes in diets and living habits in recent years, the uptake of high-protein and high-purine food is increased, along with the amount of gout patients, whose number has grown twice by the last 20 years (Jones D P et al., Med Pediatr Oncol, 1990, 18: 283-286). In a survey on gout patients around the Huangpu River (in Shanghai) in 1998, the incidence rate of hyperuricemia has grown to 10.1%, and that of gout to 0.34%, which is similar with the gout incidence rate in America of last 80s to 90s (0.275%-1.000%) (Chen S et al., Clin Med J., 1998, 111 (3): 228-230). Patients with hyperuricemia only need to control their diets if no clinical symptom occurs; however, with clinical symptom caused by hyperuricemia, medication will be necessary. Tools for conventional clinical therapy include: anti-inflammatory and analgesic drugs, such as colchicine, buprofen, naproxen, etc., which can control cute episode of gouty arthritis and eliminate local pain, swelling and inflammation of joint; uricosuric agents promoting the excretion of uric acid (invalid for lowered kidney function), such as probenicid, sulfinpyrazone, benzbromarone, etc.; as well as uric acid synthesis inhibitors, such as allopurinol. Allopurinol is most commonly used in treating patients suffering from gouty deposition, kidney insufficiency, leukemia and some genetic diseases, wherein it can inhibit xanthine oxidase and disable the transformation of hypoxanthine and xanthine into uric acid, and be oxidated in vivo to oxipurinol that is soluble and can be expelled with urine. However, chronic gout patients with gouty deposition can hardly be cured by all kinds of routine treatment. Additionally, after long-term uptake of the above medicines, patients will inevitably exhibit complications such as neutropenia, impaired heart function, liver and kidney dysfunction, digestive system stimulation, glycosuria caused by aplastic anemia, as well as gout, etc.

Human hyperuricemia is relevant to uricase gene mutation in the human evolution, wherein a terminator codon is induced in advance (Wu X et al., Proc. Natl. Acad. Sci. USA, 1989, 86: 9412-9416), thus disabling the human ability to synthesize active uricase and terminating the human purine catabolism at uric acid (Wu X et al., J. Mol. Evol., 1992, 34: 78-84). Urate with lower solubility (about 11 mg/100 mL water) can be transformed to more soluble allantoin (about 147 mg/100 mL water) by active uricase in the liver peroxisome of non-human primates and other mammals, hence being more effectively excreted by kidney (Wortmann R L, Kelley W N, Kelley's Textbook of Rheumatology (6 th), 2001: 1339-1376). In western countries, uricase prepared by *Aspergillus flavus* (Uricozyme) have been used in treating tumor chemotherapy-related hyperuricemia for more than 10 years (Zittoun R et al., Ann. Med. Interne., 1978, 127: 479-482). ELITEK, a drug of recombinant *Aspergillus flavus* uricase produced by *Saccharomyces cerevisiae* fermentation in Sanofi Corp., France, has been granted by FDA in 2002 and been used in the short-term treatment of severe hyperuricemia from tumor chemotherapy (Pui C H et al., Leukemia, 1997, 11: 1813-1816.). Meanwhile, ELITEK has been proved to be able to reduce the volume of gouty deposition after injection (Potaux L et al., Nouv. Presse. Med., 1975, 4: 1109-1112).

Uricase (EC 1.7.3.3) exists extensively in microorganisms (such as *Bacillus fastidiosus, Candida mycoderma* and *Aspergillus flavus*), plants (such as beans and chickpeas), and animals (such as pigs, cows, dogs, and papios) (Suzuki K et al., J. Biosci. Bioeng., 2004, 98: 153-158). It can catalyse the oxidation of uric acid to allantoin at the presence of oxygen, releasing carbon dioxide (Retailleau P et al., Acta. Cryst. D., 2004, 60: 453-462).

The active uricase is a tetramer protein with identical subunits, each having molecular weight of about 34 kD and consisting of 301-304 amino acids. Uricase has maximum enzymatic activity at pH 8.0 (Bayol A et al., Biophys. Chem., 1995, 54: 229-235). Among all origins, uricase has the highest activity from *Aspergillus flavus*, which is up to 27 IU/mg; the second highest from *Bacillus fastidiosus* with 13 IU/mg (Huang S H et al., Eur. J. Biochem., 2004, 271: 517-523). Additionally, bean-origined uricases have activities of merely 2-6 IU/mg. As for recombinant expressed mammal uricases, the activity of pig uricase can reach 5 IU/mg, and papio uricase only 1 IU/mg (Michael H et al., 2006, U.S. Pat. No. 7,056,713B1); while human uricase has no activity.

Studies on recombinant uricase for human application are mainly focused on high activities of microorganism uricases and low immunogenicities of mammal uricases. However,

*Aspergillus flavus* uricase shares less than 40% of homology with hypothetic human uricase (Lee C C et al., Science, 1988, 239: 1288-1291), and easily provokes antibody from human body. Therefore, the effect of *Aspergillus flavus* uricase is weakened rapidly and severe anaphylactic reaction is initiated, making it impossible for long-term treatment. Although the human uricase gene is disabled by mutation, the immunogenicity of the enzyme would be reduced if the gene was reformed and the activity recovered. However, because of missense mutations accumulated during the evolution, it is difficult to recover the human uricase activity by amino acid mutations.

Among many patent publications and literatures about mammal uricase, pig-papio chimeric uricase is studied by Duke University and Savient Corp. (Michael H et al., 2006, U.S. Pat. No. 7,056,713B1), wherein 1-9 arginines is substituted with lysines in the full-length pig uricase sequence while retaining the activity, to facilitate the following PEG modification. The PEG-ylated pig-papio chimeric uricase achieves lower immunogenicity in human bodies.

Provided herein is another novel mammal uricase with one part of human uricase amino acid sequence introduced at the C-terminal, wherein the mammal uricase exhibits lower immunogenicity while retaining the enzymatic activity. A series of studies have proved that the mammal uricase and mutants thereof have improved stability in vivo and are suitable in drug compositions for the treatment of hyperuricemia-related diseases.

DESCRIPTION OF DRAWINGS

FIG. 1: Alignment of different mammal uricase amino acid sequences.

FIG. 4: SDS-PAGE (A) (from left: Band 1, marker; and Band 2, UHC protein after purification) and RP-HPLC (B) of the purified UHC chimeric protein.

DETAILED DESCRIPTION

Figure 2:
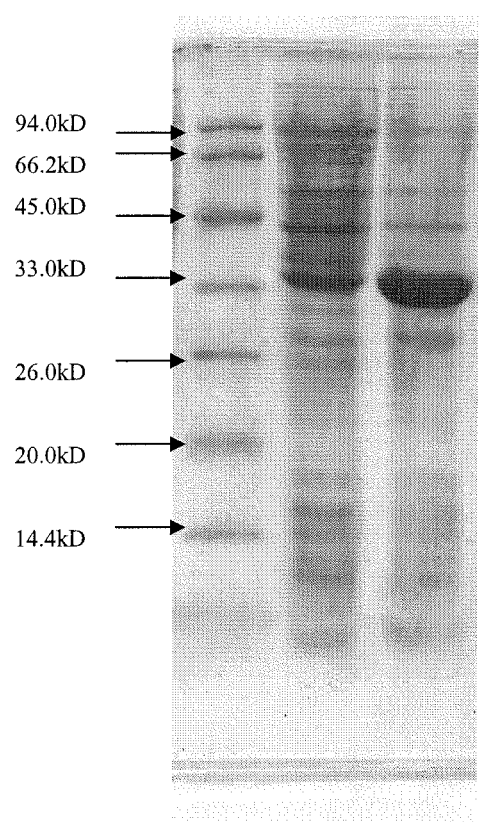
FIG. 2: SDS-PAGE of recombinant expressed UHC chimeric protein (from left: Band 1, the marker; Band 2, the control; and Band 3, induction for 4 hours)

The aim of the invention is to provide a novel mammal uricase, wherein the uricase is a chimeric protein that comprises amino acids of non-human mammal uricase and amino acids of human uricase, and mutants thereof.

Another aim of the invention is to provide DNA molecule encoding said chimeric protein and mutants thereof, vector comprising the DNA sequence, and host cell comprising the vector.

Yet another aim of the invention is to provide a cheap and/or convenient method for preparing said chimeric protein that comprises amino acids of non-human mammal uricase and amino acids of human uricase, and mutants thereof.

Yet another aim of the invention is to provide a protein drug that can reduce the uric acid concentration in blood and can be used in the treatment of hyperuricemia and gout caused thereby.

In the first aspect of the invention, provided is a chimeric protein that comprises amino acids of non-human mammal uricase and amino acids of human uricase, and mutants thereof More specifically, the first 240 amino acids at the N-terminal of said chimeric protein are amino acids 1-240 of non-human mammal uricase, namely pig, dog, cow, etc.; and the following 64 amino acids are amino acids 241-304 of human uricase. Mutants of said chimeric protein comprise at least one of the following mutations: Leu245 replaced by His, Ser246 replaced by Thr, Ser248 replaced by Gly, Arg249 replaced by Gin, Ala252 replaced by Glu, Ile253 replaced by Met, and Phe266 replaced by Leu. Preferably, mutants are selected from sequences comprising 2-5 mutations as followings: S246T-S248G-R249Q; L245H-A252E-I253M; S246T-S248G-R249Q-F266L; and L245H-A252E-I253M-F266L (which are presented in triplet form of letter-number-letter, wherein numbers stand for locations of amino acids mutated, the former letters stand for original amino acids and the latter for amino acids substituting the former; wherein L stands for Leu, S for Ser, T for Thr, G for Gly, Q for Gin, A for Ala, E for Glu, I for Ile, M for Met, F for Phe, and R for Arg). Also provided is the C- and/or N-terminal truncated form of the above chimeric protein and mutants thereof. Preferably, 1-8 amino acids are truncated at the N-terminal, and 1-3 amino acids at the C-terminal, by which the protein exhibits better stability against degradation.

In the second aspect of the invention, provided is DNA molecule encoding the above chimeric protein and mutants thereof.

In the third aspect of the invention, provided is expression vector comprising the above DNA molecule, and method of constructing the expression vector.

In the fourth aspect of the invention, provided is host cell comprising the above expression vector and possible method for transform or transfection thereof.

In the fifth aspect of the invention, provided is method for preparing the recombinant chimeric protein of the invention and mutants thereof, including steps of: expressing said protein in the host cell under conditions suitable for the expression; and separating and purifying said protein.

In the sixth aspect of the invention, provided is drug composition of said recombinant chimeric protein of uricase and mutants thereof, comprising pharmaceutically acceptable vectors, excipients or diluents, as well as effective dose of the chimeric protein of the invention.

Amino acids of mammal uricase, such as dog, pig, cow, goat etc., share more than 88% identities and highly uniformed active regions with that of human uricase (FIG. 1). Therefore, a chimeric protein can be made by substituting part of non-active amino acids of human uricase into the amino acid sequence of non-human mammal uricase, to retain the original activity as well as to improve the homology with human uricase, thus reducing immunogenicity in human body.

The inventor finds that amino acids 241-304 of human uricase exhibit no significant effect towards the activity. Hence, a humanized chimeric uricase can be made by chimerizing the above sequence with amino acids 1-240 at the N-terminal of uricases from dog, pig, cow or goat. The enzymatic activity of the humanized chimeric uricase is no lower than those of uricases from dog, pig, cow or goat, while the identities between the two can be increased to more than 91%, thereby reducing immunogenicity.

It is well known in the art that physical and chemical instabilities should be avoided in developing recombinant protein drugs. The biophysical properties of uricase, such as high hydrophobicity, etc., make it inevitable that relatively high concentration (>5 mg/ml) of the protein solution will accelerate the cross-linking and aggregation under non-physiological conditions, such as high temperatures or weak acidic pH values (i.e., inferior physical stability and unsuitable for preparation). The inventor has found that 2-5 amino acids mutations to the amino acid sequence of forementioned humanized uricase will enhance or improve the physical and chemical instabilities (such as reducing the hydrophobic aggregation, increasing solvent compatibility, enhancing the heat stability in vitro, and extending the half-life in vivo, etc.), while retaining the enzymatic activity.

The last 3 amino acids (SKL or SRL) of the C-terminal of mammal uricase are known to be peroxisome recognition site (Satoshi MIURA et al., Eur. J. Biochem, 1994, 223: 141-146), which is mainly used in locating the protein (in peroxisome) and contributes nothing to maintenance of the activity. Studies on uricase structures show that the above 3 amino acids are located at the surface of the three-dimensional structure and likely to be recognized by the immune system, thus provoking immune response. Therefore, immunogenicity of the protein can be further reduced in the invention by deleting the 3 amino acids at the C-terminal via recombinant technologies. Studies also show that the first 8 amino acids at the N-terminal of mammal uricases share low homologies and contribute nothing to maintenance of the activity. Therefore, immunogenicity of the protein can also be reduced in the invention by deleting the 8 amino acids at the N-terminal via recombinant technologies.

In conclusion, the invention provides a novel chimeric protein of uricase, which comprises amino acids of non-human mammal uricase and amino acids of human uricase, and mutants thereof.

As used herein, the term "amino acid sequence of human uricase" refers to amino acids 241-304 of said chimeric protein which are derived from human (SEQ ID NO: 1). The term "sequence of mammal uricase" refers to amino acids 1-240 of said chimeric protein which are derived from uricase amino acid sequences of pig (SEQ ID NO: 2), dog (SEQ ID NO: 3), or cow (SEQ ID NO: 4), wherein the dog uricase is preferred.

As used herein, the term "mutants" refers to proteins with one or several amino acid substitutions, or truncations at the N- and/or C-terminal, in the above chimeric proteins; while remaining bioactivities.

The mutant comprises at least one of the following substitutions: Leu245 replaced by His, Ser246 replaced by Thr, Ser248 replaced by Gly, Arg249 replaced by Gln, Ala252 replaced by Glu, Ile253 replaced by Met, or Phe266 replaced by Leu. Preferably, mutants are selected from the following sequences comprising 2-5 mutations: S246T-S248G-R249Q; L245H-A252E-I253M; S246T-S248G-R249Q-F266L; or L245H-A252E-I253M-F266L (which are presented in triplet form of letter-number-letter, wherein numbers stand for locations of amino acids mutated, the former letters stand for original amino acids and the latter for amino acids substituting the former). Also provided is the C- and/or N-terminal truncated form of the above chimeric protein and mutants thereof. Preferably, 1-8 amino acids are truncated at the N-terminal, and 1-3 amino acids at the C-terminal.

In a preferred embodiment of the invention, provided is a recombinant dog-human chimeric uricase (UHC), wherein the first 240 amino acids at the N-terminal of the chimeric protein (SEQ ID NO: 5) are amino acids 1-240 of dog uricase, and the following 64 amino acids are amino acids 241-304 of human uricase. The peptide shares 91.4% of identity with human uricase amino acid sequence (SEQ ID NO: 1), and has 112% of activity when compared to dog uricase.

In another preferred embodiment of the invention, mutants refer to at least one of the following amino acid substitutions in the chimeric protein UHC, namely: Leu245 replaced by His, Ser246 replaced by Thr, Ser248 replaced by Gly, Arg249 replaced by Gln, Ala252 replaced by Glu, Ile253 replaced by Met, or Phe266 replaced by Leu. Preferably, mutants are selected from the following sequences comprising 2-5 mutations: S246T-S248G-R249Q (SEQ ID No: 6); L245H-A252E-I253M (SEQ ID No: 7); S246T-S248G-R249Q-F266L (SEQ ID No: 8); or L245H-A252E-I253M-F266L (SEQ ID No: 9) (which are presented in triplet form of letter-number-letter, wherein numbers stand for locations of amino acids mutated, the former letters stand for original amino acids and the latter for amino acids substituting the former). The above mutants can enhance physical and chemical properties (such as reducing the hydrophobic aggregation, increasing solvent compatibility, enhancing the heat stability in vitro, and extending the half-life in vivo, etc.).

In yet other preferred embodiments of the invention, provided are mutants with N- and/or C-terminal truncated forms of the above chimeric protein and mutants thereof, e.g., truncation of amino acids 2-7 at the N-terminal and deletion of Lys9 (SEQ ID NO: 10); truncation of amino acids 302-304 at the C-terminal (SEQ ID NO: 11); and truncations at both the N-terminal and the C-terminal (SEQ ID NO: 12).

The invention further provides polynucleotide of RNA or DNA encoding the above chimeric protein and mutants thereof, wherein the DNA includes cDNA; genomic DNA and artificially synthesized DNA. The DNA can be double-stranded or single-stranded. Sequences encoding chimeric protein of the invention and mutants thereof may not be the same due to the redundancy and degeneracy of the genetic code.

Polynucleotides encoding the above chimeric protein and mutants thereof may be obtained by methods well known in the art, such as DNA recombination and PCR, etc. For example, the method may include, but not limit to, double stagger extension PCR used in a preferred embodiment and site-directed mutation described in the Quickchange of St antagene.

Polynucleotides encoding the above chimeric protein and mutants thereof may include: encoding sequence of the chimeric protein and mutants thereof; encoding sequence of the chimeric protein and mutants thereof as well as additional encoding sequences (such as leader or secretion sequence, or proprotein sequence); encoding sequence of the chimeric protein and mutants thereof as well as non-coding sequences (such as introns or non-coding sequences at the 5' and/or 3'-terminal of the encoding sequence). Therefore, the term "polynucleotides encoding the chimeric protein and mutants thereof" refers to polynucleotides that may not only comprise encoding sequences of the chimeric protein and mutants thereof, but also additional encoding sequences and/or non-coding sequences.

Polynucleotide of the invention is inserted into expression vector and transformed or transducted into host cells to be expressed. Said vector can be replicated in the form of episome or intergrated into the chromosome of the host cell. Under the control of suitable promotors, the uricase chimeric protein and mutants thereof may be expressed in mammalian cells, insects, yeasts, bacteria or other cells, or be obtained from non-cell translation systems using RNAs derived from DNA constructor of the invention. Preferably, polynucleotides of the invention are cloned in *E. coli*. Other suitable host microorganisms include *Bacillus subtilis*, *Serratia* sp., *Pseudomonas* sp. and *Staphylococcus* sp., etc. Expression vector can also be prepared in the above prokaryotic host cell, which may comprise any one of the known promotors, such as Lac promotor system, Trp promotor system, β-lactamase promotor system, or phage λ or T7 promotors. Usually, promotors control the expression, and initiate and accomplish the transcription and translation with ribosome binding site sequence, etc.

Other microorganisms, such as yeasts or fungi, etc., may also be used for the expression. Preferred yeast host cells are

*Pichia pastoris, Saccharomyces cerevisiae, Schizosaccharomyces pombe* and *Pichia angusta*. Suitable fungi include *Aspergillus niger, Trichoderma reesei* and *Schizophyllum commune*, and other fungi can also be used.

Protein of the invention may also be produced by cultivating mammalian cells. Preferred cells include: CHO cell line, multiple COS cell lines, NSO cell, Syrian Hamster ovary cell line, Hela cell or human embryo kidney cell line (i.e., HEK293, HEK293EBNA).

The vector comprising target polynucleotide (such as chimeric protein of uricase and mutants thereof, as well as control sequence) can be transformed into host cell by methods known in the art, depending on the type of the host cell. For example, calcium chloride transformation is usually used for procaryotic cells, while calcium phosphate treatment or electroporation is often suitable for other host cells.

The obtained recombinant chimeric protein of uricase and mutants thereof can be separated from inside or outside (such as culture medium) of host cell, and be purified to high purity. The purification method is not limited to any specific method. Actually, any one of purification methods known in the art may be used, such as column chromatography, e.g., affinity chromatography, ion-exchange column chromatography, hydrophobic chromatography, gel filtration chromatography, reverse phase chromatography, and adsorption chromatography; filtration; ultrafiltration; salt fractionation; isoelectric point precipitation; dialysis; etc. Chromatography may be carried out with liquid chromatography such as HPLC and FPLC. Common protein assay methods such as HPLC, SDS-PAGE, isoelectric focusing, BCA, Lowry, and Western Blot, etc., can be used to detect the concentration and purity of proteins. Therefore, recombinant chimeric uricase and mutants thereof with high purity can be provided by the invention.

The invention is described in details thereto, and can be further illustrated with reference to the following examples, which are not meant to limit the present invention.

EXAMPLES

Example 1

Recombinant Expression of Human-Dog Chimeric Uricase UHC in *E. Coli*

In this example, the involved chimeric protein comprised the first 240 amino acids at the N-terminal from dog uricase sequence, and the 241-304 from human uricase amino acid sequence. The above nucleotide sequence was synthesized according to the code preference of *E. coli* by TaKaRa Biotechnology (DaLian) co., ltd. The nucleotide sequences were as follows: (Seq ID NO: 13):

```
CAT ATG GCC CAT TAT CAT AAT GAT TAT AAA AAA AAT
GAT GAA GTT GAA TTT GTT CGT ACC GGT TAT GGT AAA
GAT ATG GTT AAA GTT CTG CAT ATT CAG CGT GAT GGT
AAA TAT CAT TCT ATT AAA GAA GTT GCC ACC TCT GTT
CAG CTG ACC CTG TCT TCT AAA AAA GAT TAT GTT TAT
GGT GAT AAT TCT GAT ATT ATT CCA ACC GAT ACC ATT
AAA AAT ACC GTT CAT GTT CTG GCC AAA TTT AAA GGT
ATT AAA TCT ATT GAA ACC TTT GCC ATG AAT ATT TGT
```
-continued
```
GAA CAT TTT CTG TCT TCT TTT AAT CAT GTT ATT CGT
GCC CAG GTT TAT GTT GAA GAA GTT CCA TGG AAA CGT
TTT GAA AAA AAT GGT GTT AAA CAT GTT CAT GCC TTT
ATT CAT AAT CCA ACC GGT ACC CAT TTT TGT GAA GTT
GAA CAG ATG CGT TCT GGT CCA CCA GTT ATT CAT TCT
GGT ATT AAA GAT CTG AAA GTT CTG AAA ACC ACC CAG
TCT GGT TTT GAA GGT TTT ATT AAA GAT CAG TTT ACC
ACC CTG CCA GAA GTT AAA GAT CGT TGT TTT GCC ACC
AAA GTT TAT TGT AAA TGG CGT TAT CAT CAG GGT CGT
GAT GTT GAT TTT GAA GCC ACC TGG GAT ACC GTT CGT
GAT ATT GTT CTG GAA AAA TTT GCC GGT CCT TAT GAT
AAA GGT GAA TAT TCT CCA TCT GTT CAG AAA ACC CTG
TAT GAT ATT CAG GTT CTG TCT CTG TCT CGT GTT CCA
GCC ATT GAA GAT ATG GAA ATT TCT CTG CCA AAT ATT
CAT TAT TTT AAT ATT GAT ATG TCT AAA ATG GGT CTG
ATT AAT AAA GAA GAA GTT CTG CTG CCA CTG GAT AAT
CCT TAT GGT AAA ATT ACC GGT ACC GTT AAA CGT AAA
CTG TCT TCT CGT CTG TGA TAA GGA TCC
```

The recombinant plasmid was entirely synthesized and amplified, and digested with NdeI and BamHI. The target fragment was recovered and inserted by T4 DNA ligase into plasmid pET-3C (Invitrogen) which was also digested with NdeI and BamHI, and resulting products were transformed into *E. coli* DH5α using standard methods described in, e.g., "Current Protocols in Molecular Biology".

Transformants were cultured overnight in LB/AMP plates and single colony was picked to prepare the plasmid. Recombinant plasmid pET-3C-UHC was screened by enzymatic digestion and PCR amplification, and the sequence from positive plasmid was testified to be identical with that of chimeric protein UHC by DNA sequencing (TaKaRa, DaLian). The above plasmid was transformed into *E. coli* expression strain to be expressed.

*E. coli* BL21 (DE3), BL21 Star (DE3) or BL21 Star (DE3) plysS were used to express UHC chimeric protein. These strains were merely some of those suitable for the expression, which were commercially available from Novagen, Invitrogen or Stratagen, respectively. Transformants could be identified by their abilities to grow at LB plates containing AMP.

The recombinant *E. coli* comprising UHC recombinant plasmid was cultured overnight in liquid LB containing 50 μm/ml of AMP, and the culture solution was innoculated by 1:25-1:200 into a large scale culture. After cells were grown to a certain optical density at 600 nm, IPTG was added to a final concentration of 0.4 mM for induction expression, followed by further culture of 3-12 hours. Cells were harvested by centrifugation, washed with 50 mM Tris buffer, preserved at $-20^L$, and then subjected to SDS-PAGE assay (FIG. 2).

Example 2

Construction of Mutant DNA of Human-Dog Chimeric Uricase UHC and the Recombinant Expression in E. Coli

Figure 3:
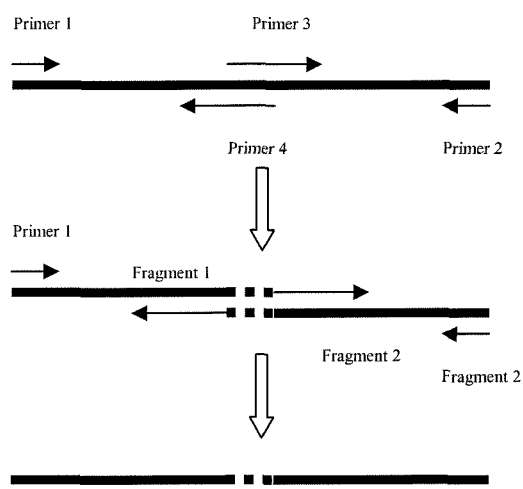
FIG. 3: Stagger extension PCR process
Figure 5:
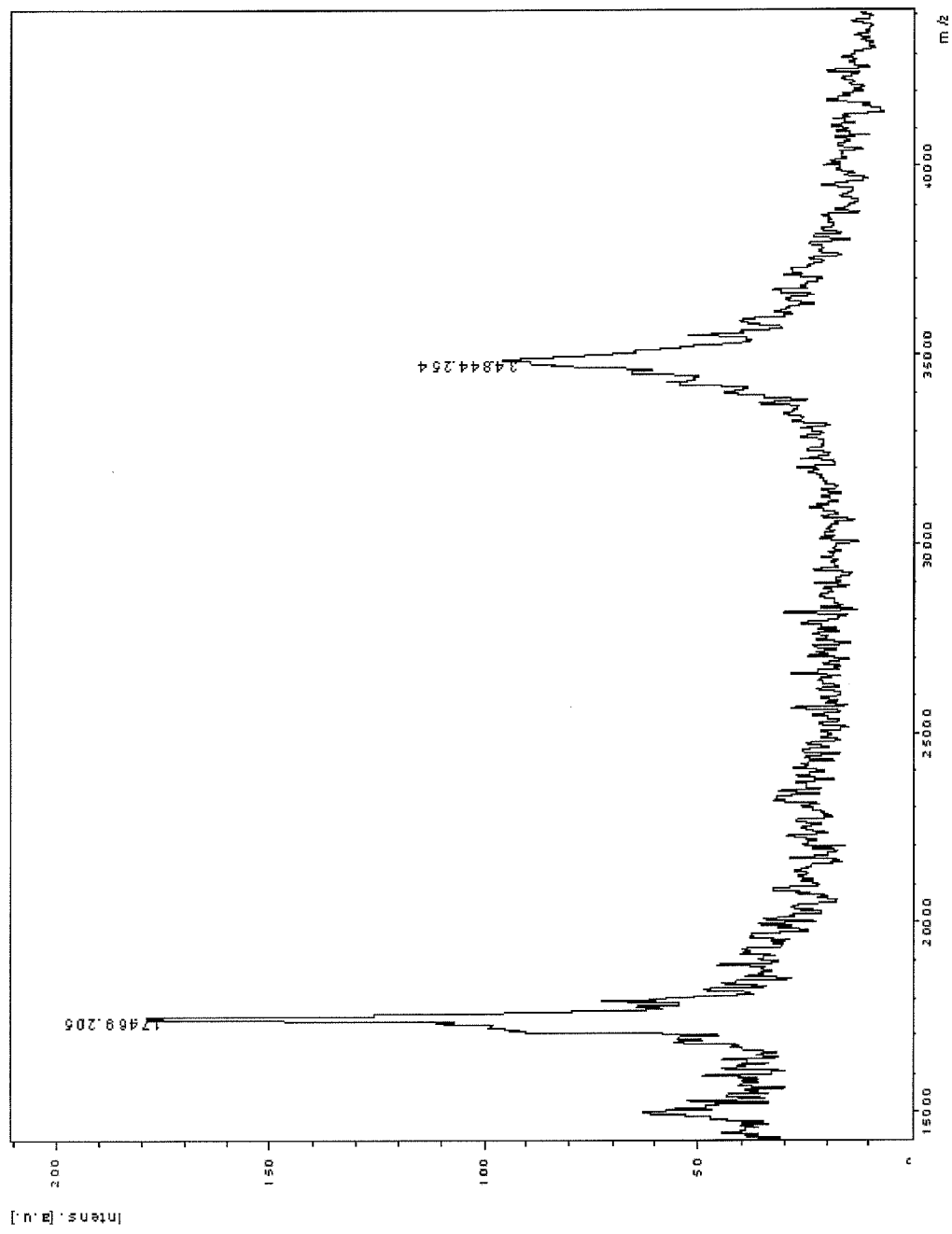
FIG. 5: Mass spectrum of purified UHC chimeric protein.

DNAs comprising target mutants were prepared using UHC DNA sequence as an original template by stagger extension PCR (FIG. 3). S246T-S248G-R249Q and S246T-S248G-R249Q-F266L were prepared as examples.

| Primers | DNA sequences |
|---|---|
| Primer 1 (Seq ID NO: 14) | 5' CACGACATATGGCCCATTATCATA 3' |
| Primer 2 (Seq ID NO: 15) | 5' GGATCCTTATCACAGACGAGAA 3' |
| Primer 3 (Seq ID NO: 16) | 5' TCTCTGTCTCGTGTTCCAGAAATGGAAGATATGGAAATTTCT 3' |
| Primer 4 (Seq ID NO: 17) | 5' TTCTGGAACACGAGACAGAGAATGAACCTGAATATCATACAG 3' |
| Primer 5 (Seq ID NO: 18) | 5' TTCATTATCTGAATATTGATATGTCTAAAA 3' |
| Primer 6 (Seq ID NO: 19) | 5' ATCAATATTCAGATAATGAATATTTGGCAG 3' |
| Primer 7 (Seq ID NO: 20) | 5' CGCAT ATG TAT AAA AAT GAT GAA G 3' |
| Primer 8 (Seq ID NO: 21) | 5' GT GGA TCC TTA TCA AGA CAG TTT A 3' |

Preparation of $UHC_{245/252/253}$: PCR Phase 1:

$UHC_{245/252/253}$-a fragment was obtained using the sequence synthesized in Example 1 (Seq ID NO: 8) as a template, and Primer 1 and Primer 3 in Table 2 as primers, wherein a PCR kit (TaKaRa, DaLian) was used according to the instruction of manufacturer under conditions of 94° C. 1 min, 56° C. 1 min, and 72° C. 1 min for 30 cycles, with denaturation of 94° C. 10 min at the first cycle, and extension of 72° C. 10 min at the last; PCR phase 2: $UHC_{245/252/253}$-b fragment was obtained by amplification with the above PCR process using the same template as in PCR phase 1, and Primer 2 and Primer 4 as primers; PCR phase 3: $UHC_{245/252/253}$ (SEQ ID NO: 7) was obtained by amplification with the above PCR process using a 1:1 mixed solution of $UHC_{245/252/253}$-a fragment and $UHC_{245/252/253}$-b fragment as a template, and Primer 1 and Primer 2 as primers.

Preparation of $UHC_{245/252/253/266}$: PCR Phase 1:

$UHC_{245/252/253/266}$-a fragment was obtained by amplification with the above PCR process using the $UHC_{245/252/253}$ (SEQ ID NO: 7) as a template, and Primer 1 and Primer 5 in Table 2 as primers; PCR phase 2: $UHC_{245/252/253/266}$-b fragment was obtained by amplification with the above PCR process using the same template as in PCR phase 1, and Primer 2 and Primer 4 as primers; PCR phase 3: $UHC_{245/252/253/266}$ (SEQ ID NO: 9) was obtained by amplification with the above PCR process using a 1:1 mixed solution of $UHC_{245/252/253/266}$-a fragment and $UHC_{245/252/253/266}$-b fragment as a template, and Primer 1 and Primer 2 as primers.

Preparation of $\Delta N\text{-}UHC_{245/252/253}$, $\Delta C\text{-}UHC_{245/252/253}$, and $\Delta NC\text{-}UHC_{245/252/253}$:

$\Delta N\text{-}UHC_{245/252/253}$ (SEQ ID NO: 10) was obtained by amplification with the above PCR process using the $UHC_{245/252/253}$ (SEQ ID NO: 9) as a template, and Primer 7 and Primer 2 in Table 2 as primers; $\Delta C\text{-}UHC_{245/252/253}$ (SEQ ID NO: 11) was obtained by amplification with the above PCR process using $UHC_{245/252/253}$ (SEQ ID NO: 8) as a template, and Primer 1 and Primer 8 as primers; and $\Delta NC\text{-}UHC_{245/252/253}$ (SEQ ID NO: 12) was obtained by amplification with the above PCR process using $\Delta N\text{-}UHC_{245/252/253}$ (SEQ ID NO: 10) as a template, and Primer 1 and Primer 8 as primers.

The 5'-terminals of Primer 1, 7 and Primer 2, 8 comprise restriction enzyme cutting sites of NdeI and BamHI, respectively. DNA sequences comprising mutants were digested with NdeI and BamHI, followed by enzymatic ligation, transformation and expression, with same methods as in Example 1.

Example 3

Purification of UHC Chimeric Protein and Mutants thereof Expressed in E. Coli

50 g of cell precipitate was added into a 500 ml lysis solution (pH 8.2, 25 mM Tris-HCl and 0.1 mg/ml lysozyme), and stirred at 37° C. for 2 hours, then subjected to ultrasonic waves (500W for 4S, intervals for 6 S, 30 cycles) and centrifugation. The supernatant was abandoned and the precipite was dissolved by 2 L of $Na_2CO_3$ (0.1M, pH 10.2), followed by stirring overnight at room temperature and centrifugating. The precipitate was abandoned and the supernatant was supplemented with 15% saturated ammonium sulfate, precipitated at 4° C. for 2 hours; and centrifugated. The supernatant was abandoned and the precipite was dissolved by 2 L of $Na_2CO_3$ (0.1M, pH 10.2), followed by stirring overnight at room temperature and centrifugating. The precipite was abandoned and the supernatant was subjected to QAE agarose anion-exchange column chromatography (GE). After entirely loaded, the target protein was linearly eluted with 0-0.5 M of NaCl (pH 10.2, 0.1 M $Na_2CO_3$) and washed out at 0.3 M. The eluted component was purified with Sephacryl S 200 molecular sieve and the main peak was collected, which was the target protein peak. The above component was then subjected to xanthine affinity chromatography (Sigma), wherein the component was diluted with 0.1 M $Na_2CO_3$ (pH 10.2) to 0.5 mg/ml and uploaded, and eluted with 0.1 M of $Na_2CO_3$ (pH 10.2) containing 60 µm of xanthine. The result of SDS-PAGE and HPLC assay showed that the purity was over 95% (FIG. 4).

Example 4

Assays on the Activity of UHC Chimeric Protein and Mutants Thereof

One international unit (IU) of uricase was defined as the enzyme amount that can transform 1 µmol of uric acid to allantoin in one minute under the condition of 25° C. and pH 8.5. Uric acid has a characteristic absorption peak at 293 nm, while the product after degradation by uricase has no absorption peak. Therefore, the change of absorbance at 293 nm was detected regularly to determine the decrease of uric acid. Uric acid concentration was calculated from its molar extinction coefficient ($1.23 \times 10^4$ $M^{-1} \cdot CM^{-1}$), and thereby determining the uricase activity. An ultraviolet spectrophotometer was pre-heated at 293 nm and 0.1 M of sodium tetraborate solution was used as a blank to set zero. 3 mL of 0.1 mM uric acid solution was added into a cuvette and 10-50 μl of UHC chimeric protein and mutants thereof were added, respectively. The absorbance was recorded every 30 seconds to detect the change at OD293 in 3 min. Concentration of uric acid at different time point was calculated according to formular C=A/Kb (C: uric acid concentration, A: absorbance in 293 nm, K: molar extinction coefficient $1.23 \times 10^4$ $M^{-1} \cdot CM^{-1}$, b: inner diameter of the cuvette); decrease of uric acid was calculated according to formular ΔM=ΔCV (ΔM: decrease of uric acid, ΔC: change of uric acid concentration, C: volume of the solution); and uricase activity was calculated according to formular U=ΔM/TV1 (U: uricase activity unit in one milliliter of plasma, T: reaction time (min), V1: volume of the UHC chimeric protein and mutants thereof).

| Proteins | Specific activities, of enzymes (IU/mg) |
|---|---|
| Dog uricase | 5.6 |
| UHC | 6.3 |
| UHC$_{246/248/249}$ | 7.1 |
| UHC$_{246/248/249/266}$ | 7.3 |
| UHC$_{245/252/253}$ | 6.9 |
| UHC$_{245/252/253/266}$ | 6.8 |
| ΔN- UHC$_{245/252/253}$ | 6.7 |
| ΔC- UHC$_{245/252/253}$ | 6.8 |
| ΔNC- UHC$_{245/252/253}$ | 6.7 |

Example 5

Stabilities of UHC Chimeric Protein and Mutants Thereof In Vitro

Stability against hydrophobic aggregation: 1 mg/ml of UHC, UHC$_{246/248/249}$, UHC$_{246/248/249/266}$, UHC$_{245/252/253}$ and UHC$_{245/252/253/266}$ were respectively incubated at 4° C. for 12 hours, and the absorbance was detected at 280 nm and 350 nm. Aggregation index was calculated according to formular AI=100×OD$_{350}$/(OD$_{280}$−OD$_{350}$) for each protein (Table 3), and the specific activity retention was detected.

| Proteins | Aggregation index | Specific activity retention |
|---|---|---|
| Dog uricase | 21.3 | 77.6% |
| UHC | 20.5 | 79.5% |
| UHC$_{246/248/249}$ | 11.3 | 91.2% |
| UHC$_{246/248/249/266}$ | 10.2 | 90.5% |
| UHC$_{245/252/253}$ | 15.7 | 85.3% |
| UHC$_{245/252/253/266}$ | 16.2 | 83.9% |

Thermostability: 1 mg/ml of UHC, UHC$_{246/248/249}$, UHC$_{246/248/249/266}$, UHC$_{245/252/253}$ and UHC$_{245/252/253/266}$ were respectively incubated at 30° C. for 5 days, and detected for the specific activity retention.

| Proteins | Specific activity retention |
|---|---|
| Dog uricase | 55.1% |
| UHC | 60.3% |
| UHC$_{246/248/249}$ | 65.5% |
| UHC$_{246/248/249/266}$ | 67.8% |
| UHC$_{245/252/253}$ | 71.2% |
| UHC$_{245/252/253/266}$ | 69.8% |

Example 6

Stabilities of UHC Chimeric Protein and Mutants Thereof In Vivo 20 of eared rabbits (New Zealand) of 2.0-2.5 kg were divided randomly into 5 groups, each intravenously injected with different kinds of UHC chimeric proteins and mutants thereof, respectively, with a dosage of 1.0 mg/kg. Blood was sampled at 1, 3, 6, 12 and 24 hour, anticoagulated with 3.2% of trisodium citrate, and centrifugated at 12000 rpm for 10 min. Supernatant plasma was taken for assays of activities and pharmacokinetics. AUCs were calculated for different groups as followings.

| Proteins | AUC (activity × hours) |
|---|---|
| Dog uricase | 3.11 |
| UHC | 3.26 |
| UHC$_{246/248/249}$ | 4.11 |
| UHC$_{246/248/249/266}$ | 4.53 |
| UHC$_{245/252/253}$ | 4.78 |
| UHC$_{245/252/253/266}$ | 3.99 |

Example 7

Pharmacodynamics In Vivo

From 70 roman hens of 100 days, 15 were randomly selected as blank controls (normal feed and free for water drinking), and the other 55 were fed with model establishing feeds (corn flour as bed charge, supplemented with fish flour and bone meal, wherein the protein content was over 20%, and calcium over 4%) and limited water of no more than 100 mL per day. After 2-3 weeks of model establishment, roman hens with blood uric acid concentration of more than 480 μmol/L were taken as hyperuricemia models (45 hens), and were randomly divided into 3 groups, 15 hens each, comprising: UHC uricase group, with UHC subcutaneously injected by 1 mg/kg once a day; positive control group, with benzbromarone fed by 5 mg/kg once a day; and the control, with model establishing feeds. After 3 weeks of drug administration, blood was sampled from veins of chicken wing and uric acid concentration was determined with a uric acid kit as followings:

| Groups | Blood uric acid concentration, 0 day after drug administration (μm/L) | Blood uric acid concentration, 10 days after drug administration (μm/L) | Blood uric acid concentration, 21 days after drug administration (μm/L) |
|---|---|---|---|
| Normal | 234 ± 15 | 241 ± 29 | 220 ± 34 |
| UHC | 529 ± 123 | 411 ± 78 | 266 ± 69 |
| Benzbromarone | 527 ± 109 | 455 ± 67 | 416 ± 98 |
| Control | 534 ± 136 | 551 ± 121 | 520 ± 131 |

Results showed that the blood uric acid level was significantly reduced in hyperuricemia animals after UHC protein injection.

The invention claimed is:

1. A humanized recombinant uricase, wherein the humanized recombinant uricase is a chimeric protein which comprises amino acids of non-human mammal uricase and amino acids of human uricase, wherein the first 240 amino acids at the N-terminal of said chimeric protein are amino acids 1-240 of non-human mammal uricase and the following 64 amino acids are amino acids 241-304 of human uricase.

2. The humanized recombinant uricase according to claim 1, wherein said non-human mammal is selected from the group consisting of dog, pig, goat and cow.

3. The humanized recombinant uricase according to claim 2, wherein said non-human mammal uricase is dog uricase with an amino acid sequence of SEQ ID NO: 5.

4. The humanized recombinant uricase according to claim 2, wherein said chimeric protein is selected from proteins with substitution, deletion or addition of 1-8 amino acids in said chimeric protein, while still maintaining uricase activity.

5. The humanized recombinant uricase according to claim 4, wherein said chimeric protein comprises at least one of the following mutations:
   Leu245 replaced by His;
   Ser246 replaced by Thr;
   Ser248 replaced by Gly;
   Arg249 replaced by Gln;
   Ala252 replaced by Glu;
   Ile253 replaced by Met; and
   Phe266 replaced by Leu.

6. The humanized recombinant uricase according to claim 5, wherein said chimeric protein comprises at least one of the following mutations that are presented in triplet form of letter-number-letter, wherein numbers stand for the location of amino acids mutated, the former letters stand for original amino acids and the latter for amino acids substituting the former:
   S246T-S248G-R249Q;
   L245H-A252E-I253M;
   S246T-S248G-R249Q-F266L;
   L245H-A252E-I253M-F266L.

7. The humanized recombinant uricase according to claim 6, having an amino acid sequence selected from the group consisting of SEQ ID NO: 6, SEQ ID NO: 7, SEQ ID NO: 8 and SEQ ID NO: 9.

8. The humanized recombinant uricase according to claim 4, wherein said chimeric protein is truncated at the N-terminal by 1-8 amino acids.

9. The humanized recombinant uricase according to claim 4, wherein said chimeric protein is truncated at the C-terminal by 1-3 amino acids.

10. The humanized recombinant uricase according to claim 8, having an amino acid sequence of SEQ ID NO: 10.

11. A drug composition comprising:
   pharmaceutically acceptable vectors, excipients or diluents; and
   an effective dose of the humanized recombinant uricase of claim 1.

12. A method for treating diseases, comprising:
   administering to a subject in need of such treatment an effective amount of the humanized recombinant uricase of claim 1, wherein said diseases include hyperuricemia and gout caused thereby.

13. The humanized recombinant uricase according to claim 9, having an amino acid sequence of SEQ ID NO: 11.

14. The humanized recombinant uricase according to claim 4, wherein said chimeric protein is truncated at the N-terminal by 1-8 amino acids and at the C-terminal by 1-3 amino acids.

15. The humanized recombinant uricase according to claim 14, having an amino acid sequence of SEQ ID NO: 12.

16. The humanized recombinant uricase according to claim 5, wherein said chimeric protein is selected from at least one of the following mutations that are presented in triplet form of letter-number-letter, wherein numbers stand for the location of amino acids mutated, the former letters stand for original amino acids and the latter for amino acids substituting the former:
   L245H-A252E-I253M;
   L245H-A252E-I253M-F266L.

17. The humanized recombinant uricase according to claim 16, having an amino acid sequence selected from the group consisting of SEQ ID NO: 7 and SEQ ID NO: 9.

* * * * *